US009545219B2

(12) United States Patent
Moussavi et al.

(10) Patent No.: US 9,545,219 B2
(45) Date of Patent: Jan. 17, 2017

(54) ACOUSTIC SYSTEM AND METHODOLOGY FOR IDENTIFYING THE RISK OF OBSTRUCTIVE SLEEP APNEA DURING WAKEFULNESS

(71) Applicant: UNIVERSITY OF MANITOBA, Winnipeg (CA)

(72) Inventors: Zahra Moussavi, Winnipeg (CA); Davood Karimi, Winnipeg (CA)

(73) Assignee: University of Manitoba, Winnipeg (CA)

(*) Notice: Subject to any disclaimer, the term of this patent is extended or adjusted under 35 U.S.C. 154(b) by 768 days.

(21) Appl. No.: 13/679,897

(22) Filed: Nov. 16, 2012

(65) Prior Publication Data
US 2014/0142452 A1    May 22, 2014

(51) Int. Cl.
*A61B 5/08*    (2006.01)

(52) U.S. Cl.
CPC .................... *A61B 5/0826* (2013.01)

(58) Field of Classification Search
CPC ... A61B 5/0826; A61B 5/4806; A61B 5/4809; A61B 5/4818
USPC ........................................................ 600/529
See application file for complete search history.

(56) References Cited

U.S. PATENT DOCUMENTS

| | | | | |
|---|---|---|---|---|
| 6,669,651 B1* | 12/2003 | Fukushima | ............ | A61B 3/112 351/200 |
| 2003/0060725 A1* | 3/2003 | Kline | ...................... | A61B 5/08 600/529 |
| 2013/0253357 A1* | 9/2013 | Moussavi | ............ | A61B 5/4818 600/529 |

FOREIGN PATENT DOCUMENTS

WO    WO 2011/154791 A2 * 12/2011

OTHER PUBLICATIONS

A.Azarbarzin and Z.Moussavi, "Nonlinear properties of snoring sounds," Proc. ICASSP, Prague, pp. 4316-4319, 2011 (A & M).*

(Continued)

*Primary Examiner* — Michael Kahelin
*Assistant Examiner* — Mitchell E Alter
(74) *Attorney, Agent, or Firm* — Valauskas Corder LLC

(57) ABSTRACT

The invention relates to a system and method for screening a patient for obstructive sleep apnea (OSA) using recordings of tracheal breathing sounds of both nose and mouth breathing in the upright and supine positions to compute characteristic features of the patient, the characteristic features being compared to the mean values of similar features of OSA and non-OSA training groups to classify a patient as OSA or non-OSA.

10 Claims, 10 Drawing Sheets

(56) References Cited

OTHER PUBLICATIONS

Azarbarzin, Ali. "Snoring sounds analysis: automatic detection, higher order statistics, and its application for sleep apnea diagnosis." (2011) (Azarbarzin).*
Montazeri et al., 'Acoustical screening for obstructive sleep apnea during wakefulness,' IEEE Eng Med Biol Soc, 2010:3662-5.
Montazeri et al., 'Assessment of obstructive sleep apnea and its severity during wakefulness,' Ann of Biomed Eng, Apr. 2012, vol. 40, No. 4, pp. 916-24. Epub Nov. 9, 2011.
Nuckton et al., 'Physical examination: mallampati score as an independent predictor of obstructive sleep apnea,' Sleep, vol. 29, No. 7, pp. 903-908, 2006.
Peng et al., 'Feature selection based on mutual information: criteria of max-dependency, max-relevance, and min-redundancy,' IEEE Transactions on pattern analysis and machine intelligence, vol. 27, No. 8, pp. 1226-1238, Aug. 2005.
Wetter et al., 'Smoking as a risk factor for sleep-disordered breathing,' Arch Intern Med, vol. 154, No. 19, pp. 2219-2224, Oct. 2004.
Young et al., 'Predictors of sleep-disordered breathing in community-dwelling adults,' Arch Intern Med, vol. 162, No. 8, pp. 893-900, Apr. 2002.

\* cited by examiner

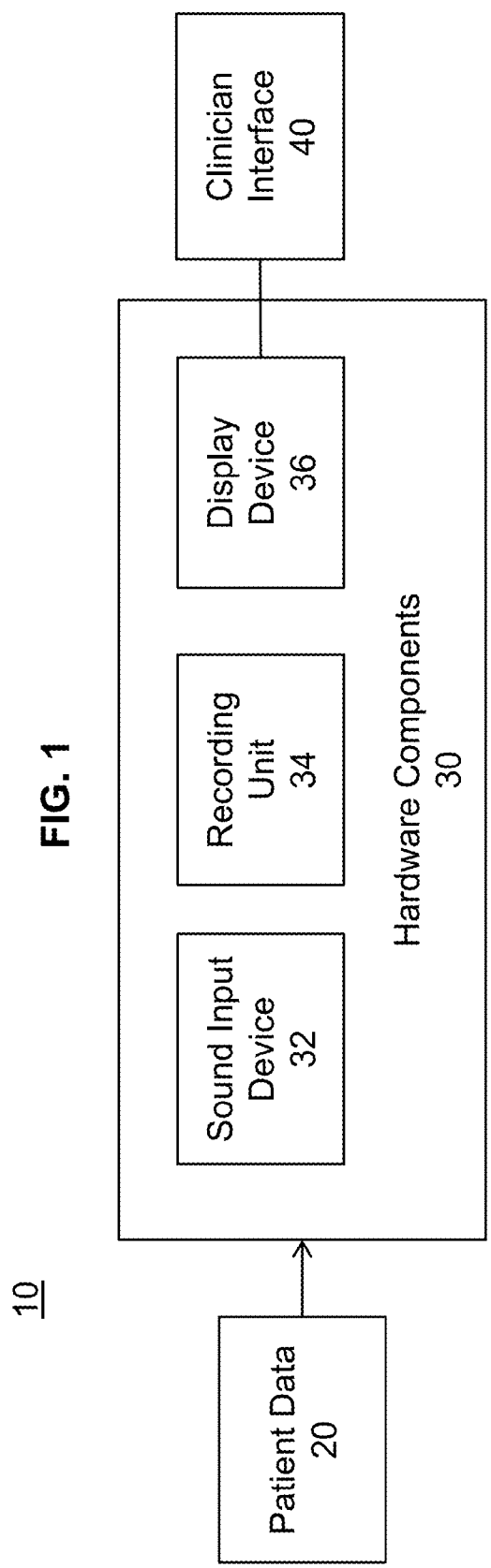

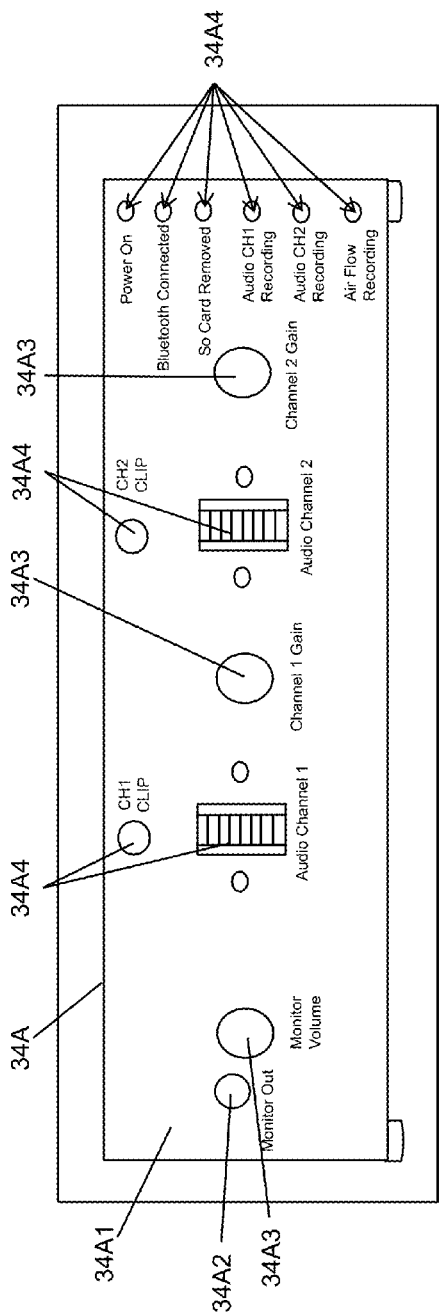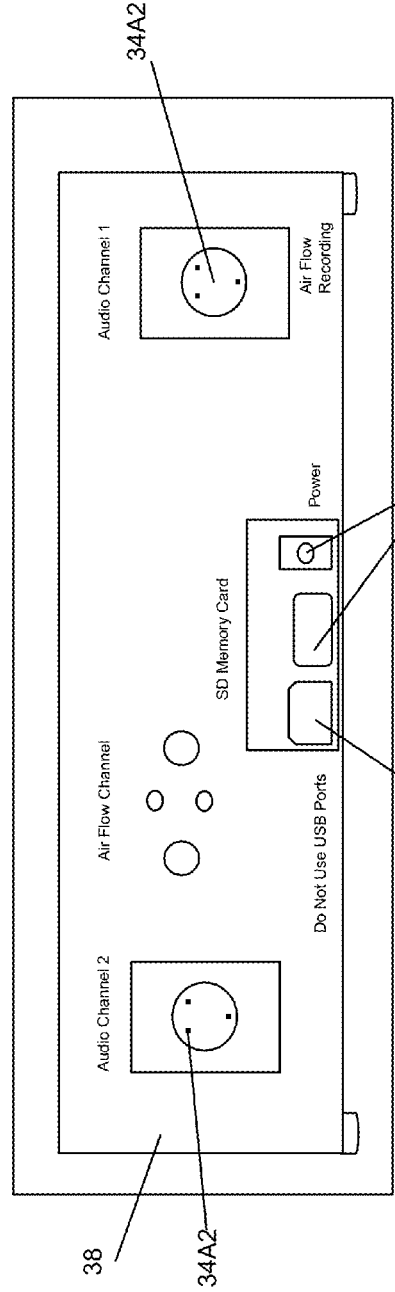
FIG. 2A
FIG. 2B

ACOUSTIC SYSTEM AND METHODOLOGY FOR IDENTIFYING THE RISK OF OBSTRUCTIVE SLEEP APNEA DURING WAKEFULNESS

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The invention relates a system and methods for screening patients for obstructive sleep apnea. The invention employs an acoustical system and methods based on collecting and analyzing tracheal sounds to detect apnea during wakefulness.

BACKGROUND OF THE INVENTION

Obstructive sleep apnea (OSA) is a common sleep disorder characterized by repetitive pharyngeal collapses resulting in extended pauses in breathing (apnea) or instances of abnormally low breathing flow (hypopnea) during sleep. Untreated OSA may result in neurocognitive impairments and cardiovascular complications including hypertension, heart failure, stroke, excessive daytime sleepiness, as well as increased risk of occupational and traffic accidents.

Severity of OSA is quantified by apnea hypopnea index (AHI), which is the number of apnea and hypopnea events per hour of sleep. An apnea event is defined as complete cessation of respiratory airflow for at least 10 s, whereas a hypopnea event is characterized by a decrease in airflow by 50% for 10 s. Apnea/hypopnea events usually result in a significant drop (>4%) in blood oxygen saturation level ($SaO_2$). In OSA, by far the most common type of sleep apnea, breathing is interrupted despite respiratory effort, because the airway is physically blocked. In central sleep apnea (CSA), the effort to breathe is weak or absent. Mixed sleep apnea is a combination of OSA and CSA.

An estimated 2-7% of women and 4-14% of men over 30 years of age have moderate to severe OSA. However, most OSA patients are not clinically diagnosed. A major study in the United States found that in a population with access to a sleep disorders clinic, more than 80% of middle-aged men and women who suffered from moderate or severe OSA had not been diagnosed. Undiagnosed OSA negatively impacts overall health and quality of life, is associated with increased risk of accidents, and is very costly to the medical system. The mean annual medical cost of an undiagnosed OSA patient is estimated to be approximately twice that of a non-OSA individual, accounting for several billion dollars in additional annual medical costs in the U.S. alone.

Currently, standard testing for OSA involves overnight polysomnography (PSG) in a sleep laboratory. PSG includes simultaneous recording of electroencephalogram, electrooculogram, electromyogram of chin and anterior tibialis, respiratory airflow, electrocardiogram, pulse oximetry, and snoring sounds. Because PSG is expensive, time-consuming, and inconvenient, many patients with OSA are not diagnosed or treated.

Thus, there is a need in the art for improved methods of diagnosing OSA. The present invention satisfies this demand.

SUMMARY OF THE INVENTION

The present invention provides a system and methods to screen a patient for OSA while the patient is in awake. The system and methods are configured to be non-invasive and provide relatively accurate screening results. In certain embodiments of the system, tracheal breath sounds of a patient are filtered, amplified, recorded, and analyzed to identify the characteristic features of the breathing sounds for a patient. Advantageously, the system and methods allow for simple screening of a patient suspected of having OSA while the patient is awake.

In certain embodiments, breath sound features characteristic of patients with OSA may be determined by analyzing processed tracheal breath sounds obtained from a group of non-OSA patients and a group of OSA patients having an AHI of <10 or an AHI of >20, respectively, as determined by PSG. Tracheal breath sound signals were obtained during wakefulness from each patient in the non-OSA and OSA groups in both supine and upright positions during nose and mouth breathing maneuvers. Power Spectrum Density (PSD) and bispectrum of the tracheal breath sound signals in each respiratory phase was calculated and normalized. The PSD of the normalized signal was estimated in the frequency range of 100 Hz to 2500 Hz, and the bispectrum was estimated in the frequency range of 100 Hz to 2500 Hz. From the estimated power spectrum density, the signal power, spectral centroid, spectral bandwidth, spectral flatness, and crest factor were computed over the whole frequency band used in power spectrum estimation, i.e. 100-2500 Hz. Additionally, the signal power, spectral centroid, and spectral bandwidth were computed for 100-150 Hz, 150-450 Hz, 450-600 Hz, 600-1200 Hz, 1200-1800 Hz, and 1800-2500 Hz sub-bands. From the estimated bispectrum, bispectral invariant parameter, average magnitude and average power of the bispectrum, normalized bispectral entropy, normalized bispectral squared entropy, sum of logarithmic amplitudes, sum of logarithmic amplitudes of diagonal elements, first and second-order moment of the logarithmic amplitudes of diagonal elements, phase entropy, median bifrequency, and average amplitude of the bispectrum over equal and non-overlapping regions in the non-redundant region were computed. Differences in feature values between nose and mouth breathing and between upright and supine breathing were computed. All features were normalized so that each had a mean of zero and a standard deviation of 1.

In certain embodiments of the invention, a non-invasive system for screening a patient for OSA includes a sound input device suitable for detecting tracheal breath sounds, e.g., a device that may be placed on the suprasternal notch of the trachea of the patient. A recording device is connected to the sound input device. The breathing sound signals are band-pass filtered by signal conditioning component to remove components below 20 Hz (removing dc) and above 2500 Hz (anti-aliasing filter), amplified, and recorded. The recorded breathing sounds from a patient are used to compute the characteristic features. The extracted features are compared with the values of the corresponding features for a group of OSA subjects and a group of non-OSA subjects. The comparison may be used to classify the subject as OSA or non-OSA. Gender, age, BMI (Body Mass Index), neck circumference, Mallampati score, smoking history, of the subject can be used to improve the accuracy of the classification.

The present invention and its methodology and advantages will be further understood and appreciated with reference to the detailed description below of presently contemplated embodiments, taken in conjunction with the accompanying drawings.

BRIEF DESCRIPTION OF THE DRAWINGS

FIG. 1 is a block diagram of a system for screening a patient for obstructive sleep apnea according to one embodiment of the present invention.

FIG. 2A illustrates a front view of an embodiment breath sound recording box.

FIG. 2B illustrates a rear view of an embodiment of a breath sound recording box.

DETAILED DESCRIPTION OF THE INVENTION

Figure 2C:
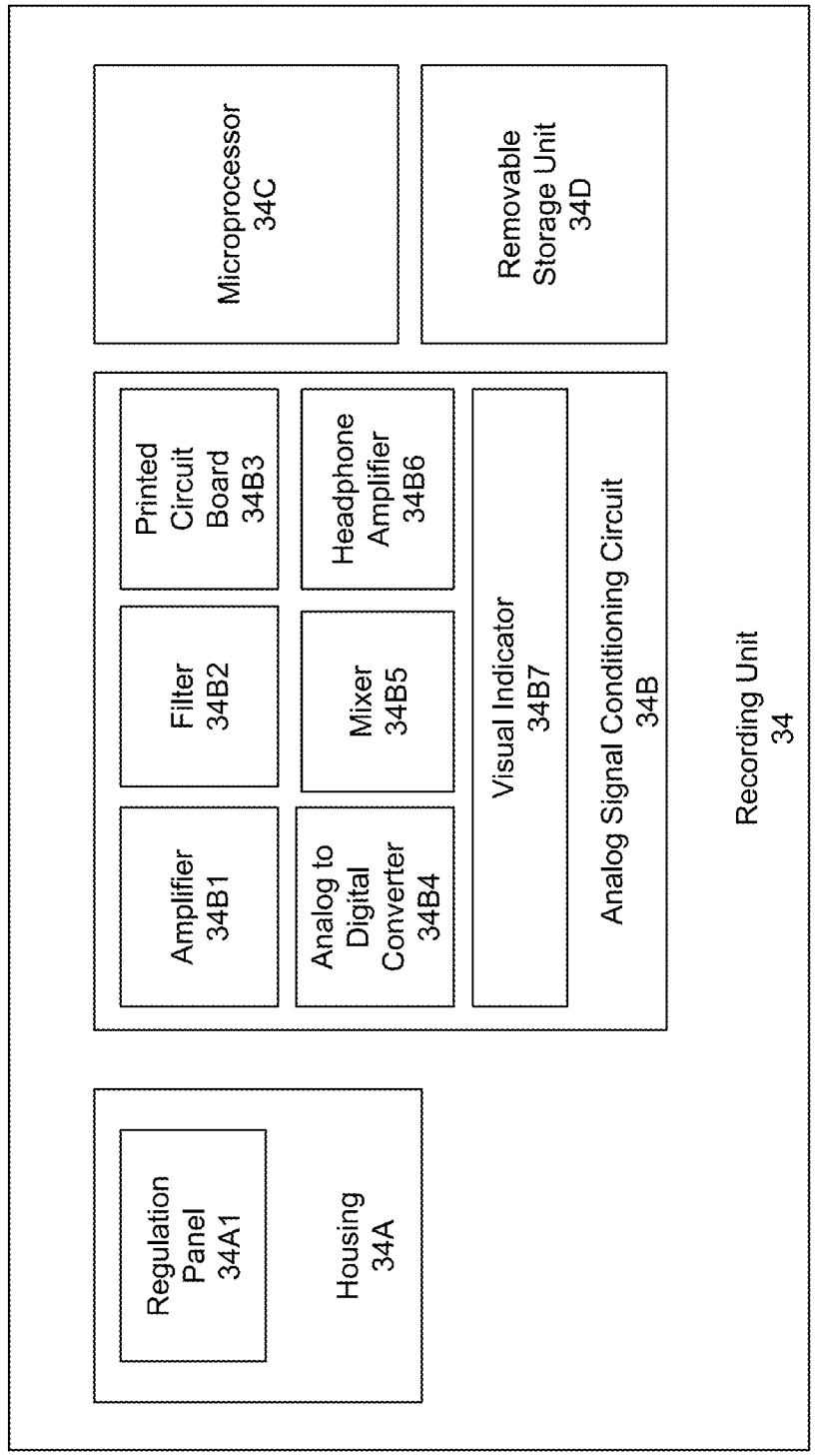
FIG. 2C is a block diagram of an embodiment of a recording unit according to the present invention.

The present invention relates to a system and methods for classifying patients as non-OSA or OSA that rely on power spectral and bispectral features of breath sounds obtained during wakefulness.

FIG. 1 illustrates the system for screening a patient for obstructive sleep apnea according to one embodiment of the present invention. The system 10 may include hardware components 30, for example, a sound input device 32, a recording unit 34, and a display device 36.

A sound input device 32 may be configured to detect tracheal breath sounds. In certain embodiments, a sound input device 32 may include a microphone.

A recording unit 34 may be configured to connect with the sound input device 32 (and possibly a pneumotachograph for other research purposes). FIG. 2A and FIG. 2B show a front view and rear view, respectively of an embodiment of a recording unit 34 configured as a sound recording box.

A recording unit 34 may include a housing 34A that includes a regulation panel 34A1, as illustrated in FIG. 2A. The regulation panel 34A1 may include a socket 34A2, one or more regulators 34A3, and one or more indicators 34A4. A regulator 34A3, such as a knob, switch, or other controller, may be configured to regulate, for example, a monitor or channel gain. The indicators 34A4 may include an light emitting diode (LED), a non-LED light, a scale, a gauge, or other indicator of status or condition of a component of the recording unit 34. As illustrated in FIG. 2B, sockets 34A2 configured to receive various plugs may be positioned on a secondary panel 38.

As illustrated in FIG. 2C, a recording unit 34 may include an analog signal conditioning circuit 34B and a microprocessor 34C or other type of processor configured to control data acquisition. Also, a recording unit 34 may include a removable Secure Device card or other removable storage unit 34D on which the input data is saved.

The analog circuit 34B may include a low-noise amplifier 34B1 and filter 34B2. The design may be contained on a custom printed circuit board (PCB) 34B3. The primary purpose of certain embodiments of an analog circuit 34B is the filtering and amplification for the three channels (two audio, one air flow in case if interested the airflow of breathing for research purposes). Either or both audio channels may feature a low-noise instrumentation amplifier with adjustable gain, followed by high pass and low pass filters. The gain for the identical audio channels may be adjustable between, for example, +20 dB and +60 dB, and between +34 dB and +79 dB for the air flow channel. The frequency bandwidth for the audio channels may be 20 Hz-5 kHz, and 0.05 Hz and 2.5 kHz for the air flow channel. These bandwidths may be selected to contain all the features that are of interest in the signals. Each channel also contains a separate high speed 16-bit analog to digital converter 34B4. The circuit 34B also may include a mixer 34B5 and headphone amplifier 34B6 so that a user can listen live to the audio channels to properly set up and monitor recording. For additional monitoring, an LED bar array or other visual indicator 34B7 may be included to give a visual indication of the signal level.

As described above, embodiments of the present invention also may include a display device 36. A display device 36 may include a monitor, touchscreen, or a computing system, such as a desktop computer system, handheld device including any small-sized computer device including, for example, a personal digital assistant ("PDA"), smart handheld computing device, cellular telephone, laptop, tablet, netbook computer, MP3 player, or hand held console. Although a tablet embodiment of a display device 36 is described below, any display device 36 may be used in place of a tablet.

Figure 3:
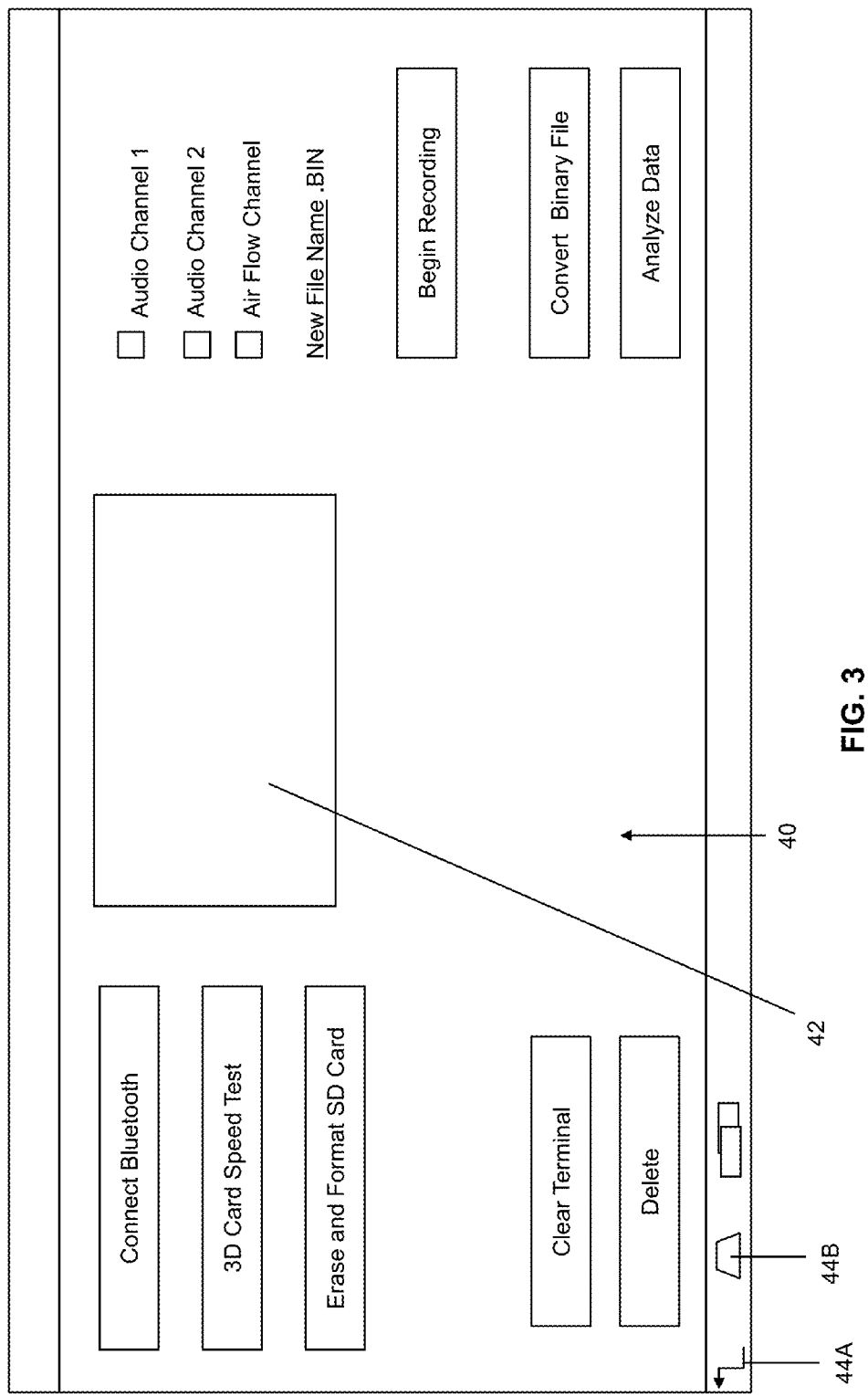
FIG. 3 is an embodiment of a user interface for the clinician for signal conditioning and data recording.

A display device 36 is configured to permit display of a user interface 40. The embodiment of a user interface 40 illustrated in FIG. 3 includes a terminal 42, and a menu 44 including a back button 44A and a home button 44B.

The acquisition of the digital data, writing to SD memory, data processing, and communication with a tablet may be all carried out by a microcontroller board. The data is read from the analog to digital converters. After the data is acquired, it is written to an SD card or other removable storage unit. The user may operate the system 10 using one or more control interfaces, such as the regulation panel 34A1 or a user interface 40. As described above, an embodiment of a regulation panel 34A1 may include a channel gain knob, monitor level indicator, and a variety of indicator LEDs.

A user may control recording, file naming, and channel selection via the user interface 40 accessed through a tablet. A simple user interface 40 provides buttons to select channels to record, start/stop recording, name the recorded files, manage and convert files contained on the SD card to any desirable format for analysis, and several other features. This interface 40 is very user friendly and easy to learn.

Figure 4A:
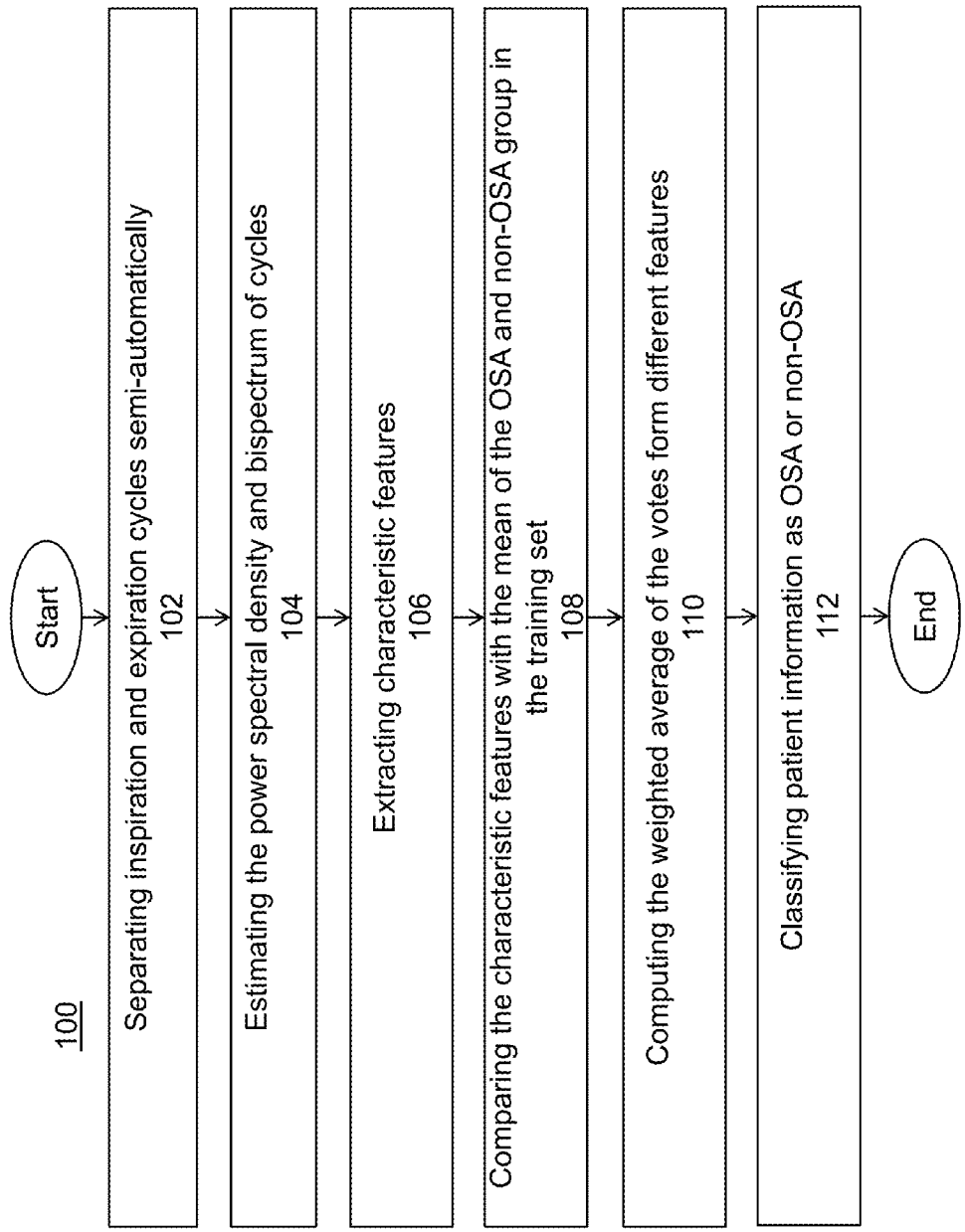
FIG. 4A illustrates an embodiment of a method according to the present invention.
Figure 4B:
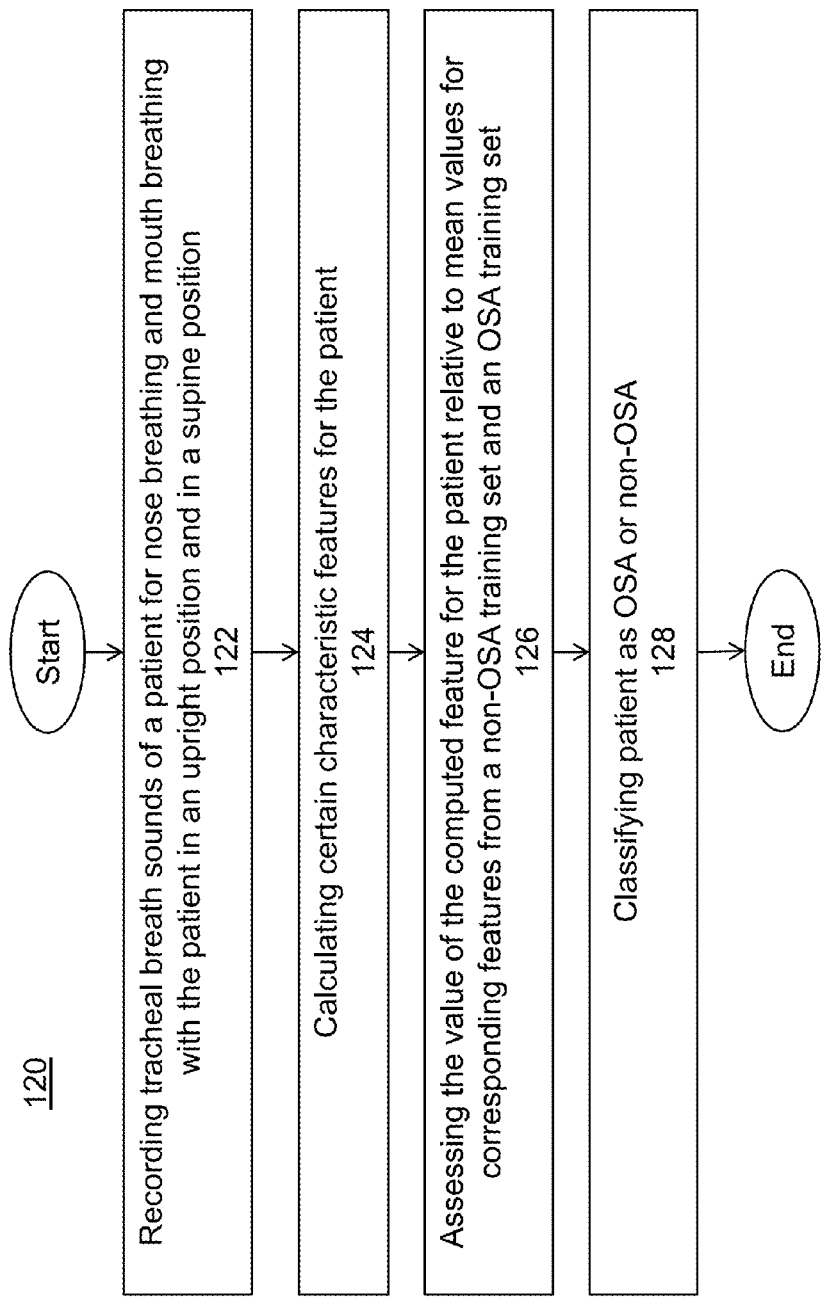
FIG. 4B illustrates an embodiment of a method according to the present invention.

FIG. 4A and FIG. 4B also illustrate a flowchart of a method 100, 120 for screening a patient for obstructive sleep apnea according to one embodiment of the present invention. The method 100 is configured to be non-invasive and permit screening a patient for obstructive sleep apnea during wakefulness. Advantageously, since the method does not need to be performed during typical sleeping periods—i.e., overnight—like many conventional methods, the present method provides a cost savings to health care facilities.

As illustrated in FIG. 4A, a method 100 may include the steps of separating inspiration and expiration cycles semi-automatically 102, estimating the power spectral density and bispectrum of cycles 104, extracting the characteristic features 106, comparing the characteristic features with the mean of the OSA and non-OSA group in the training set 108, computing the weighted average of the votes form different features 110, and classifying patient information as OSA or non-OSA 112.

As illustrated in FIG. 4B, a second method embodiment 120 may include the steps of recording tracheal breath sounds of a patient for nose breathing and mouth breathing with the patient in an upright position and in a supine position 122, calculating certain characteristic features for the patient 124, assessing the value of the computed feature for the patient relative to mean values for corresponding features from a non-OSA training set and an OSA training set 126, and classifying patient as OSA or non-OSA 128.

Breath sound characteristic features of patients with OSA are determined by analyzing tracheal breath sounds obtained from a group of non-OSA patients and a group of OSA patients having an AHI of <10 or an AHI of >20, respectively, to identify differences in features between the two groups. Tracheal breath sound signals are obtained during wakefulness from each patient in the non-OSA and OSA groups in both supine and upright positions during nose and mouth breathing maneuvers. The protocol of recording, four breathing maneuvers and deep breathing levels, may be conducted as described below. However, the order of the four trials of recordings (at different breathing maneuvers) can be interchanged. The protocol for breath sounds recording is as follows:

1. The technician/clinician or any other health care provider (or the patient in case of home device) will place the microphone (or hold the iPhone/recording device close to trachea while watching an instructing video clip in case of home device) over the suprasternal notch. First, the patient will go through a practice of normal and deep breathing (almost twice than normal breathing rate but with the same duration) while the technician/clinician (or a video clip in case of home device) will instruct them by hand for inhalation and exhalation for approximately 20 breath/minute.

2. After the short training for breathing maneuvers, 4 trials of breathing will be recorded. Subjects breathe without flow measurement but the technician/clinician (or video clip) will guide them by hand movement to keep a fixed pace (duration) and level of breathing. In all trials, it is important the recording starts with inspiration.
   I. 1st trial will be recording breathing sound for 5-6 breaths at the subject's normal flow rate followed by 5 deep breathing, while the subject is sitting upright and breathing through the nose.
   II. 2nd trial is the same as the 1st but the subject will be breathing through the mouth, with a nose clip in place. Again 5-6 breaths at normal tidal flow rate and 5-6 breaths at deep breathing.
   III. 3rd trial is the same as the 1st trial but in supine position.
   IV. 4th trial is the same as the 2nd trial but in supine position.

3. The device may automatically assign different name to every trial of data being recorded. The anthropometric information of all subjects is recorded and saved in files with the same code as the data files. For purposes of this application, the term "anthropometric information" includes age, body mass index, weight, gender, height, and other measurements of the human body and its component parts.

According to step 104, the PSD of the tracheal breath sound signals in each respiratory phase is calculated, normalized, and estimated in the frequency range of 100 Hz to 2500 Hz. From the estimated power spectrum density, the signal power, spectral centroid, spectral bandwidth, spectral flatness, and crest factor are computed over the whole frequency band, i.e. 100-2500 Hz. The signal power, spectral centroid, and spectral bandwidth are computed for 100-150 Hz, 150-450 Hz, 450-600 Hz, 600-1200 Hz, 1200-1800 Hz, and 1800-2500 Hz sub-bands.

The bispectrum is estimated in the frequency range of 100 Hz to 2600 Hz. From the estimated bispectrum, bispectral invariant parameter, average magnitude and average power of the bispectrum, normalized bispectral entropy, normalized bispectral squared entropy, sum of logarithmic amplitudes, sum of logarithmic amplitudes of diagonal elements, first and second-order moment of the logarithmic amplitudes of diagonal elements, phase entropy, median bifrequency, and average amplitude of the bispectrum over equal and non-overlapping regions in the non-redundant region are computed. Differences in feature values between nose and mouth breathing and between upright and supine breathing are computed. All features are normalized such that each have a mean of zero and a standard deviation of 1.

Many features (as many as about 900) are computed and analyzed to identify statistically significant differences (using t-test) between the non-OSA and OSA groups of two training sets. The features that are found to differ significantly between the training sets will be computed for a patient of unknown OSA status, and the patient may be classified as having or not having OSA on the basis of similarities or differences of the features to the corresponding features of OSA or non-OSA training sets. The system and methods may also be used to estimate the severity of OSA.

In a proof of concept study (described in details in the following section), for the statistical test, a data set of 70 subjects, 35 from each of the two aforementioned groups of non-OSA and OSA may be used. Some 153 features were found to be statistically significant between the two groups. Forty six of these 153 features were related to differences of the features between the nose and mouth breathing maneuvers, and 30 of the 153 features related to the difference of the features between supine and upright postures. These 46 and 30 features were often among the best combinations of features for classification.

Once the statistically significant features are determined, then using data of the same training set, the features are then sorted based on their maximum relevancy and minimum redundancy followed by an exhaustive search (floating search) to select the best combination of the features for classification. An ad-hoc classification algorithm described in details in the "Example Section" below, will then classify any data of unknown type with a relatively high accuracy. The ad-hoc classification algorithm treats every sound feature as a symptom (in the same manner that a physician considers the symptoms of a disorder) and assigns a majority vote based on each feature's classification and finally diagnose the patient's data in either OSA or non-OSA as well as an estimation of the severity of OSA.

In certain embodiments, the patients' anthropometric information is used to estimate their risk factor for having OSA. An ad-hoc classification using only the anthropometric information and associated OSA risk may be built. Certain embodiments of the system run the classification of patients with unknown condition in three parallel approaches: classification based on only sound data, based on only risk factor, and based on the results of both sound and anthropometric classifications. Furthermore, since some physicians prefer higher sensitivity versus specificity and some the other way around, the overall classification system allows tuning the algorithms for plausible different preferences of the user (i.e. a physician). The ad-hoc classification algorithm also handles the missing data in case one of the recording is too noisy and not usable, which can happen when data is recorded in uncontrolled environments such as hospitals/clinics or at homes.

The training and prediction accuracies of the classification based on breathing sound features were found to be very close, which indicates that the method is robust. Advantageously, because the measurements used in the method are quick and simple, the method is valuable in screening of OSA.

Classification based on risk factors may be less accurate and robust than the acoustic method. By choosing a proper value for the threshold, classification based on risk factors may have a high sensitivity at the cost of very low specificity. Similarly, classification results for the middle group showed that classification based on breathing sound features has relatively good specificity, whereas the methods based on risk factors have relatively low sensitivity and specificity.

In certain embodiments, methods based on breath sound features and risk factors may be combined in a method of assessing patients suspected of having OSA to provide an easy and quick screening tool. Advantageously, this may permit efficient use of limited facility and resources such as PSG by identifying individuals who are at higher risk. Currently, many of the patients referred for full-night PSG are non-OSA. For example, all of the 189 subjects in this study had been referred for PSG by a physician, but 79 (42%) were found to have an AHI of less than 5.

In one approach to combining classification based on breathing sound features and classification based on risk factors, classification based on breathing sounds is used as the primary classifier. For those patients who cannot be strongly classified as non-OSA or OSA using the primary classifier, classification based on risk factors may be performed. This approach was explored by defining the strength of an assignment by the primary classifier as the number of the votes of the winning class. For example, if four out of four features classified a subject as non-OSA, it was considered a strong classification, whereas if the votes were equally divided between the two classes and the subject was classified as non-OSA by merit of a smaller distance of the corresponding features, it was considered a weak classification. If a subject was weakly classified based on breathing sound features, classification by risk factors may also be implemented.

In another embodiment, the breath sound method and the risk factor method could be used in parallel. In other words, both of the classification methods are used for a subject and if the subject is classified as OSA by each of the two methods, the subject can be considered as having OSA or as being at high risk of having OSA and referred for further testing, e.g., PSG. This approach was explored using classification based on breathing sound features and classification based on relative risk using the same threshold computed for the training dataset. The sensitivity in identifying the subjects in the OSA (AHI>20) group for both the training and testing datasets was 94%. The specificity was 60% and 57% on training and testing datasets, respectively.

The following non-limiting examples are intended to be purely illustrative.

EXAMPLE

A Proof of Concept Study

Subjects

One hundred and eighty nine subjects participated in an exemplary study. The subjects can be divided into three groups based on AHI scores. The AHI of each of the subjects was determined through full-night PSG. Table 1 provides a description of each group and a summary of the anthropometric information for the subjects.

TABLE 1

Anthropometric information (mean ± standard deviation) for the subjects

|  | Age | BMI | Weight (kg) | Gender |
|---|---|---|---|---|
| Non-OSA (AHI < 10); n = 105 | 50.0 ± 14.8 | 31.3 ± 8.8 | 90.7 ± 27.3 | 48 F, 57 M |
| Middle group (10 ≤ AHI ≤ 20); n = 32 | 54.4 ± 12.9 | 32.3 ± 6.9 | 91.8 ± 21.2 | 13 F, 19 M |
| OSA (AHI > 20); n = 52 | 53.4 ± 11.9 | 35.2 ± 6.5 | 106.3 ± 22.5 | 7 F, 45 M |

Data Recording

Breathing sounds were recorded with an ECM77B Sony microphone. The microphone was inserted into a cylindrical plastic housing and placed on the suprasternal notch of trachea using a double-adhesive disk. The subjects were asked to breathe at their maximum respiratory flow rate at two different postures: while sitting on a chair or on the edge of the bed (upright), and while lying on his or her back on a bed (supine). At each posture, each subject was asked to first breathe through the nose, with the mouth closed. Then, each subject was asked to wear a nose clip and breathe only through the mouth. Subjects were instructed to coordinate breathing with a signal from the experimenter at a rate of approximately 17 breaths per minute. Thus, four breathing sound signals, each containing four or five breath cycles (inspiration and expiration), were obtained from each subject. The signals from the microphone were band-pass filtered to remove the frequency components below 0.05 Hz and above 5000 Hz, amplified, and recorded on a laptop computer. The sampling frequency was 10240 Hz.

For each subject, the neck circumference was measured to the nearest 1.0 cm and the Mallampati score was determined. Body mass index (BMI) was determined for each subject using height and weight measurements obtained contemporaneous with PSG testing. The subject's age, gender, and smoking history were collected from a questionnaire completed prior to PSG.

Pre-Processing of the Sound Signals and Feature Computation

Figure 5A:
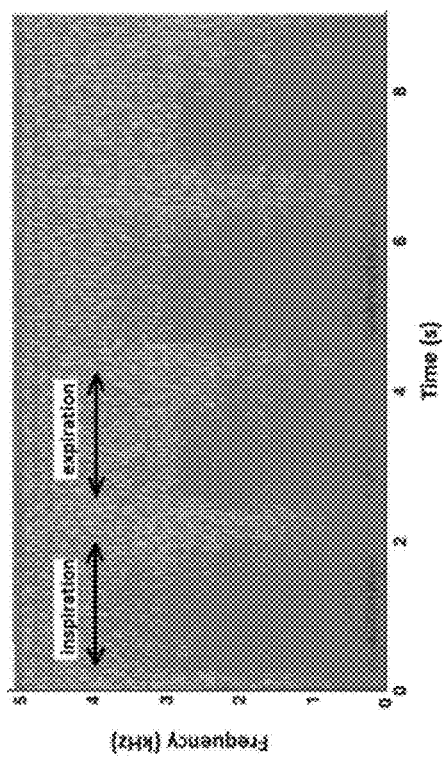
FIG. 5A is a spectrogram of a recorded tracheal breath sound signal.
Figure 5B:
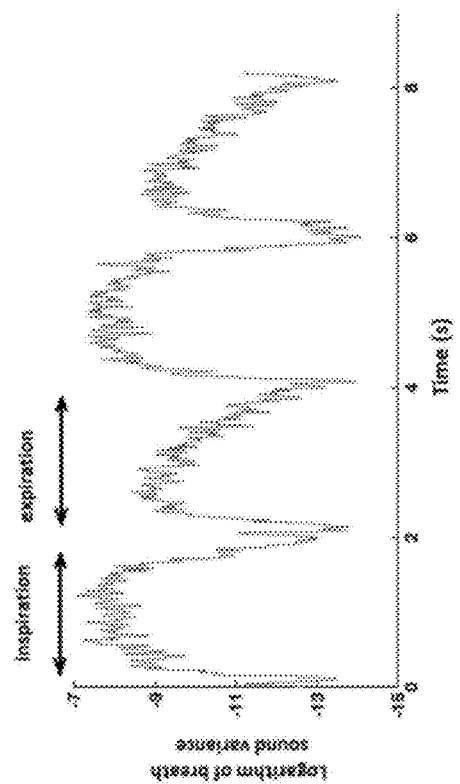
FIG. 5B is the logarithm of sound variance used to separate individual inspiration and expiration phases.

Features were computed for individual inspiration and expiration phases. Each signal contained four or five breath cycles. The first inspiration phase in each signal was marked during recording (see FIG. 5A). In order to identify and separate individual inspiration and expiration phases in each signal, logarithm of sound variance was computed in windows of 50 ms with 95% overlap (see FIG. 5B). After separating inspiration and expiration phases, the signal from each phase was divided by its standard deviation in order to minimize the effect of the difference in respiratory flow between subjects and between breathing cycles for each subject.

Power spectrum density (PSD) of the normalized signal was estimated in the frequency range of 100 Hz to 2500 Hz using the Welch estimation method with a Hamming window of 80 ms length and 50% overlap was used. The choice of the window length was made by trial and error. Windows of length 80 ms provided a good compromise between the smoothness of the estimated PSD and its frequency resolution.

From the estimated power spectrum, the following features were computed:

i. Signal power—it gives the power of the signal in the frequency band in consideration:

$$\sum_{f=f_u}^{f=f_l} P(f)\Delta f$$

where P(f) is the estimated PSD and $f_u$ and $f_l$ represent the upper and lower limits of the given frequency band.

ii. Spectral centroid—it finds the weighted average frequency of the area under the PSD for a given frequency band. Therefore, this feature can identify the location of major peaks, if any.

$$\frac{\sum_{f=f_u}^{f=f_l} fP(f)\Delta f}{\sum_{f=f_u}^{f=f_l} P(f)\Delta f}$$

iii. Spectral bandwidth—it finds the weighted average of the squared distance between different frequency components and the spectral centroid, SC, with the weight being the value of the estimated PSD at each frequency.

$$\frac{\sum_{f=f_u}^{f=f_l} (f - SC)^2 \cdot P(f)\Delta f}{\sum_{f=f_u}^{f=f_l} P(f)\Delta f}$$

iv. Spectral flatness—also called tonality coefficient; it quantifies how tone-like a signal is, as opposed to being noise-like. For a completely flat power spectrum, i.e. white noise, it evaluates to 1. As shown by the following equation, spectral flatness is computed as the ratio of the geometric mean to the arithmetic mean of the PSD.

$$\frac{\left(\prod_{f=f_u}^{f=f_l} P(f)\right)^{\frac{1}{f_u-f_l}}}{\frac{1}{f_u - f_l}\sum_{f=f_u}^{f=f_l} P(f)\Delta f}$$

v. Crest factor—it is another measure of tonality of the signal. In other words, it can be used to distinguish between wideband signals (with smaller crest factor) and narrowband signals (with a larger crest factor).

$$\frac{\max(P(f))}{\frac{1}{f_u - f_l}\sum_{f=f_u}^{f=f_l} P(f)\Delta f}$$

Features 1 to 3 were computed for the whole frequency band used in power spectrum estimation, i.e. 100-2500 Hz, as well as for six sub-bands: 100-150 Hz, 150-450 Hz, 450-600 Hz, 600-1200 Hz, 1200-1800 Hz, and 1800-2500 Hz. Features 4 and 5 were computed for 100-2500 Hz. Furthermore, the relative power in each of the sub-bands was computed by dividing the signal power in that sub-band by the power in the band of 100-2500 Hz.

Bispectrum of each inspiration or expiration cycle was estimated using the conventional direct method, which is an approximation of bispectrum for the time series with limited available samples.

From the estimated bispectrum, the following features were extracted:

i. Bispectral invariant parameter:

$$P(a) = \operatorname{atan}\left(\frac{I_i(a)}{I_r(a)}\right)$$

where $$I(a) = I_r(a) + iI_i(a) = \int_{f_1=0^+}^{\frac{1}{1+a}} C_3(f_1, af_1)\, df_1$$

with $C_3(f_1, f_2)$ is the Fourier transform of the $3^{rd}$ order cumulant ($c3(\tau_1, \tau_2)$):

$$C_3(f_1, f_2) = \sum_{\tau_1=-\infty}^{+\infty} \sum_{\tau_2=-\infty}^{+\infty} c_3(\tau_1, \tau_2)\exp\{-2\pi j(f_1\tau_1 + f_2\tau_2)\},$$

For a zero-mean signal, the $3^{rd}$ order cumulant is equal to the third-order moment defined by:

$$c_3(\tau_1,\tau_2)=m_3(\tau_1,\tau_2)=E\{X(K)X(K+\tau_1)X(K+\tau_2)\}$$

I(a) The non-redundant region corresponds to a range of $0 < a \leq 1$. P(a) may be estimated on radial lines with a slope of 1° to 45° with 1° intervals. The integration was approximated using the technique suggested in [5].

Specifically, the integral on above is approximated as $$I(a) = \sum_{k=1}^{\lfloor(\frac{N}{2}-1)/(1+a)\rfloor} C_3(k, ak)$$

The bispectrum is interpolated as:

$$C_3(k,ak)=pC_3(k,\lfloor ak\rfloor)+(1-p)C_3(k,\lceil ak\rceil)$$

where $p=ak-\lfloor ak\rfloor$, $\lfloor x\rfloor$ represents the largest integer contained in x and $\lceil x\rceil$ represents the smallest integer that is larger than x. k references an index as the sum implies and a is a number chosen between 0 and 1.

ii. Average magnitude of the bispectrum in the non-redundant region, computed as:

$$M_{avg}=1/N\Sigma_{\Omega}|C_3(f_1,f_2)|,$$

where $\Omega$ indicates the non-redundant region.

iii. Average power of the bispectrum in the non-redundant region:

$$P_{avg}=1/N\Sigma_{\Omega}|C_3(f_1,f_2)|^2$$

iv. Normalized bispectral entropy:

$$E_1=-\Sigma_n \log p_n,$$

where $$p_n = \frac{|C_3(f_1, f_2)|}{\sum_{\Omega} |C_3(f_1, f_2)|}$$

v. Normalized bispectral squared entropy:

$$E_2=-\Sigma_n \log q_n \log q_n,$$

where $$q_n = \frac{|C_3(f_1, f_2)|^2}{\sum_{\Omega} |C_3(f_1, f_2)|^2}.$$

vi. Sum of logarithmic amplitudes:

$$H_1=\Sigma_{\Omega}\log(|C_3(f_1,f_2)|)$$

vii. Sum of logarithmic amplitudes of diagonal elements of the bispectrum:

$$H_2=\Sigma_{\Omega}\log(|C_3(f,f)|)$$

viii. First-order moment of the logarithmic amplitudes of diagonal elements:

$$H_3=\Sigma f \cdot \log(|C_3(f,f)|)$$

ix. Second-order moment of the logarithmic amplitudes of diagonal elements:

$$H_4=\Sigma (f-H_3)^2 \cdot \log(|C_3(f,f)|)$$

x. Phase entropy of the estimated bispectrum:

$$P_e=\Sigma_n p(\psi_n)\log(p(\psi_n))$$

where $$p(\psi_n) = \frac{1}{N}\sum_{\Omega} 1(\phi(C_3(f, f) \in \psi_n)),$$

$$\psi_n=\{\phi|-\pi+2\pi n/M \leq \phi \leq -\pi+2\pi(n+1)/M\}$$

xi. The median bifrequency—as the name suggests, median bifrequency is the frequency at which the area under the bispectrum is equal on both sides. Median bifrequencies were calculated along each frequency dimension of the non-redundant region of the bispectrum using the following approach:

a. The sum of all values of the bispectrum for all bifrequencies in the non-redundant region was calculated.

b. The value of $f_1$ was set to the smallest value in the non-redundant region.

c. The sum of bispectral values for all bifrequencies ($f_1$, $f_2$) in the non-redundant region was calculated.

d. If the sum calculated above was greater than half of the sum calculated in step (a), then the value of $f_1$ was taken as the median frequency for the first dimension. Otherwise, $f_1$ was incremented by 5 Hz (the frequency resolution of the estimated bispectrum) and steps (c) and (d) were repeated. The sum in step (c) was calculated accumulatively with previous runs. Similar steps were repeated for the second dimension of the bispectrum to obtain the median bifrequency in the $f_2$ direction.

xii. Average amplitude of the bispectrum over equal and non-overlapping regions in the non-redundant region was computed. Specifically, the frequency band of 100-2600 Hz in each of the $f_1$ and $f_2$ frequency axes was divided into 10 equal non-overlapping sub-bands, each extending 250 Hz in frequency. This partitioned the non-redundant region into a set of square-shaped regions (triangle-shaped for regions on the diagonal). The average amplitude of the bispectrum over each of these regions was computed.

After computing the features for individual inspiration and expiration phases for each of the four breath sound signals, they were averaged to give one feature value for inspiration and one for expiration. Further, the differences in feature values between nose and mouth breathing and between upright and supine breathing were computed. In addition, all features were normalized so that each had a mean of zero and a standard deviation of 1. Normalization of the features was necessary to ensure that all features were given equal weight in feature selection and classification steps because, as described later, feature selection and classification steps often included computing the difference between feature values and comparing them across features.

Feature Selection

A total of 912 features were computed for each subject. Subsets of features with the high classification power were identified. For this step, 35 of non-OSA subjects (AHI<10) and 35 of the OSA subjects (AHI>20) were randomly selected. Feature selection was carried out in two steps. First, for each of the 912 features, a two-tailed t-test was performed to see if the value of the feature was significantly different between the non-OSA and OSA groups. A total of 153 features were significantly different at p=0.05 level.

For each of the 153 features, a simple threshold classifier was built to classify the same 70 subjects. Then, the area under the receiver operating characteristics (ROC) curve was computed by changing the value of the threshold. Six of the 153 features had an area under the ROC curve that was less than 0.50. These features are removed because they lack classification power. This left 147 features for the next steps.

Next, small subsets of these 147 features were evaluated to determine accuracy in classifying the 70 subjects. To evaluate combinations of two features, a classification was performed on all possible pairs of features from the 147 features, using a leave-one-out scheme. To classify each subject, the feature values for that subject were compared to the mean of the feature values for the non-OSA and OSA groups. For each feature, a vote was given in favor of the group whose mean was closer to the feature value for the subject being classified. The subject was assigned to the class with more votes. If both classes received the same number of votes, the distances between the feature values for the subject and the mean of the feature values for the two classes were computed. The feature with a smaller distance received a stronger vote and was used to assign the class label to the subject being classified. The classification accuracy for all combinations of two features was thus computed.

Finally, the combination that gave the highest classification accuracy was proposed as the best combination of two features. The same approach was used to evaluate combinations of three and four features.

An exhaustive search of all possible feature combinations, from among the 147 features, is very time consuming and computationally expensive; in certain embodiments, sets of 4 features combinations were conducted. In order to choose features sets of size 5 or larger through exhaustive search, it was necessary to significantly reduce the number of features from 147. For this purpose, the Minimal-redundancy-maximal-relevance (mRMR) method [1] was employed. This method is a filter-type feature selection method that selects features with maximum relevancy to the class labels but also with minimum redundancy among themselves. The mRMR algorithm sorts the features based on minimal-redundancy-maximal-relevance criterion. The top 45 features from this method were used to choose best feature subsets of size 5, 6, and 7 exhaustively; the top 30 features were used to choose best feature subsets of size 8, 9, and 10 exhaustively. Numbers 45 and 30 were chosen so that the exhaustive search to determine the best feature subsets of size 5 to 10 could be completed in less than 48 hours on a PC with a 1.73-GHz processor.

Classification

Combinations of features selected in the previous step were used to classify the subjects that had not been used in feature selection steps. The classification approach was the same as the method described in feature selection step. Classification errors were evaluated using a leave-one-out method. There were 70 subjects in the non-OSA group and 17 subjects in the OSA group that had not been used in the feature selection steps. In addition, the 32 subjects in the middle group were also classified.

Classification Based on Relative Risk

In order to compare the accuracy of classification based on breathing sounds with the accuracy based solely on risk factors, subjects were classified into non-OSA and OSA groups based solely on six risk factors: age, gender, BMI, Mallampati score, neck circumference, and smoking history.

In this approach, a relative risk was computed for each subject. The computation relied on the results of other studies that have estimated the contribution of different risk factors from large populations. The contributions of age, gender, BMI, and neck circumference were identified from a large study (n=5615) on the major predictors of OSA in general population [2]. Young et al. estimated the odds ratio for several risk factors and an AHI of 15 or higher by developing multiple linear regression models. The odds ratios were used in the instant study for a model that included gender, BMI, age, and neck circumference. To include the contribution of the Mallampati score and smoking history on relative risk, the results from two other studies were used [3, 4]. The following is a summary of the results from these three studies:

Gender
Compared to women, men have an odds ratio of 1.71.
Age
Up to the age of 65, every 10-year increment in age will increase the odds ratio by a factor of 1.36. Beyond 65 years, the odds ratio will remain unchanged.
BMI
Every 5.3 kg/m² increment in BMI will increase the odds ratio by a factor that depends on age. For age in the ranges 34-45, 45-55, 55-65, 65-75, and 75-85 years, this factor is equal to 2.0, 1.8, 1.6, 1.5, and 1.3 respectively.
Neck circumference
Every 4.32 cm increment in neck circumference will increase the odds ratio by a factor of 1.48.
Smoking
The odds ratio for former smokers versus never-smokers is 1.86. Compared to never-smokers, the odds ratio for current smokers who smoke less than 20 cigarettes per day, between 20 and 40 cigarettes per day, and more than 40 cigarettes per day is 3.94, 3.25, and 6.74, respectively.
Mallampati score
Every 1-point increase in the Mallampati score increases the odds ratio approximately by a factor of 2.

The relative risk for all subjects was initialized to 1. Then, for each of the risk factors, the relative risk of the corresponding subjects was multiplied by the odds ratio for that risk factor. For example, compared with women, men have 1.71 times the odds of having an AHI of 15 or greater. Therefore, the relative risk for male subjects is multiplied by 1.71. This is not a very exact approach, because the odds ratio is not a simple ratio of probabilities, as shown in the following equation $$\text{odds ratio} = \frac{p_1/(1-p_1)}{p_2/(1-p_2)}$$

This approach disregards the (1−p) terms. This does not create a large error because the probabilities here are much smaller than 0.50. After computing the relative risk of the subjects, a simple threshold classifier was used to classify the subjects into non-OSA and OSA groups. In other words, it is expected that the OSA subjects have a higher relative risk compared to non-OSA subjects. Using the same 70 subjects that were used for selecting the most characteristic features of the sound signals, a threshold that could best separate these subjects was identified.

Classification Based on Breathing Sound Features

Subsets of 2 to 10 features from among the 147 features that resulted in the lowest classification error on the training data were identified. None of the 147 features appeared consistently in all of the subsets. However, there were clear overall patterns in terms of the types of features that were selected more often. For example, most of the selected PSD features came from the sub-bands of 150-450 Hz, 450-600 Hz, 600-1200 Hz, or from the entire frequency band of 100-2500 Hz. Regarding the bispectral features, the invariant features appeared most frequently in the best feature subsets. Moreover, the difference of the features between the nose and mouth breathing were selected quite frequently, whereas the difference of the features between the upright and supine breathing were selected less frequently. As an example, the combination of the following seven features was discovered to produce the lowest classification error on the training data set:

Spectral centroid of PSD for the band of 450-600 Hz, for expiration phase of mouth breathing in upright posture Spectral bandwidth for the band of 1200-1800 Hz, for expiration phase of mouth breathing in supine posture Difference between nose and mouth breathing in spectral centroid for the band of 100-2500 Hz, for expiration phase in supine posture Difference between supine and upright postures in signal power for the band of 100-150 Hz, for inspiration phase of mouth breathing Bispectral invariant at 15°, for inspiration phase of mouth breathing in upright posture
Bispectral invariant at 24°, for inspiration phase of mouth breathing in upright posture
Bispectral invariant at 27° for inspiration phase of mouth breathing in upright posture This subset of seven features is not unique in providing high classification accuracy. Many subsets of size 4 to 10 resulted in classification accuracies that were very close. Table 2 lists some 20 categories of features that appeared frequently in the best feature subsets.

TABLE 2

Categories of feature frequently appearing in the best feature subsets.

| Feature type | Feature description |
|---|---|
| Ordinary features | spectral centroid, mouth breathing, supine position |
| | spectral centroid, mouth breathing, upright position |
| | spectral bandwidth, nose breathing, upright position |
| | spectral bandwidth, nose breathing, supine position |
| | spectral bandwidth, mouth breathing, supine position |
| | Normalized bispectral squared entropy, mouth breathing, supine position |
| | Bispectral invariant, mouth breathing, upright position |
| Nose breathing-mouth breathing | relative signal power, upright position |
| | spectral centroid, supine position |
| | spectral centroid, upright position |
| | Normalized bispectral entropy, supine position |
| | Normalized bispectral entropy, upright position |
| | Bispectral invariant, upright position |
| Supine position-upright position | signal power, mouth breathing |
| | signal power, nose breathing |
| | relative signal power, nose breathing |
| | spectral centroid, nose breathing |
| | spectral centroid, mouth breathing |
| | median bi-frequency, nose breathing |
| | Bispectral invariant, nose breathing |

After identifying suitable combinations of features, the prediction accuracy of each subset of features was evaluated. Data from the 87 subjects in non-OSA and OSA groups not been included in feature selection or training sets was used, including 70 subjects in the non-OSA group (AHI<10) and 17 subjects in the OSA group (AHI>20). The selected subset of seven features, listed above, produced the lowest prediction errors. This set of seven features had an overall accuracy, specificity, and sensitivity of 78%, 77%, and 82%, respectively, on the testing data set. Specificity and sensitivity indicate the classification accuracy on the non-OSA and OSA groups respectively. Table 3 shows the accuracy, specificity, and sensitivity for classification based on the combination of seven features and results of classification based on risk factors.

TABLE 3

Summary of classification results for the testing data including 70 non-OSA (AHI < 10) and 17 OSA (AHI > 20) subjects.

| | Overall accuracy | Specificity | Sensitivity |
|---|---|---|---|
| Classification based on breathing sound features (best combination of four features) | 78% | 77% | 82% |
| Classification based on estimated relative OSA risk | 68% | 76% | 35% |

The combination of seven features described above was then used to classify subjects in the middle group, i.e., those with 10≤AHI≤20. Because an AHI of 15 is considered as the border between mild and moderate OSA, a classifier that could separate the subjects on the two sides of this border would be desirable. From the 32 subjects in the middle group, 16 had an AHI of below 15 and 16 had an AHI of above 15. From the 16 subjects with 10≤AHI<15, one of them did not have any of the feature values because of the noisy signals and therefore could not be classified, 10 (67%) were classified as non-OSA (AHI<10) and 5 (33%) were classified as OSA (AHI>20). From the 16 subjects with 15<AHI≤20, 7 of them (44%) were classified as non-OSA (AHI<10) and 9 of them (56%) were classified as OSA (AHI>20). Therefore, for this population, 67% of the subjects with 10≤AHI<15 and 56% of the subjects with 15<AHI≤20 were correctly classified.

Table 4 summarizes the result of classification of the middle group. In addition to the classification based on breathing sound features, results of classification based on risk factors is also provided in this table. It should be noted that, as suggested in the previous paragraph, in this table classification accuracy for subjects with 10≤AHI<15 indicates those classified as non-OSA and classification accuracy for subjects with 15<AHI≤20 indicates those classified as OSA.

TABLE 4

Summary of classification results for the subjects in the middle group.

| | Overall classification accuracy | Classification accuracy on subjects with 10 < AHI < 15 | Classification accuracy on subjects with 15 < AHI < 20 |
|---|---|---|---|
| Classification based on breathing sound features (best combination of 4 features) | 61% | 67% | 56% |
| Classification based on estimated relative OSA risk | 41% | 38% | 44% |

Classification Based on Risk Factors

Figure 6:
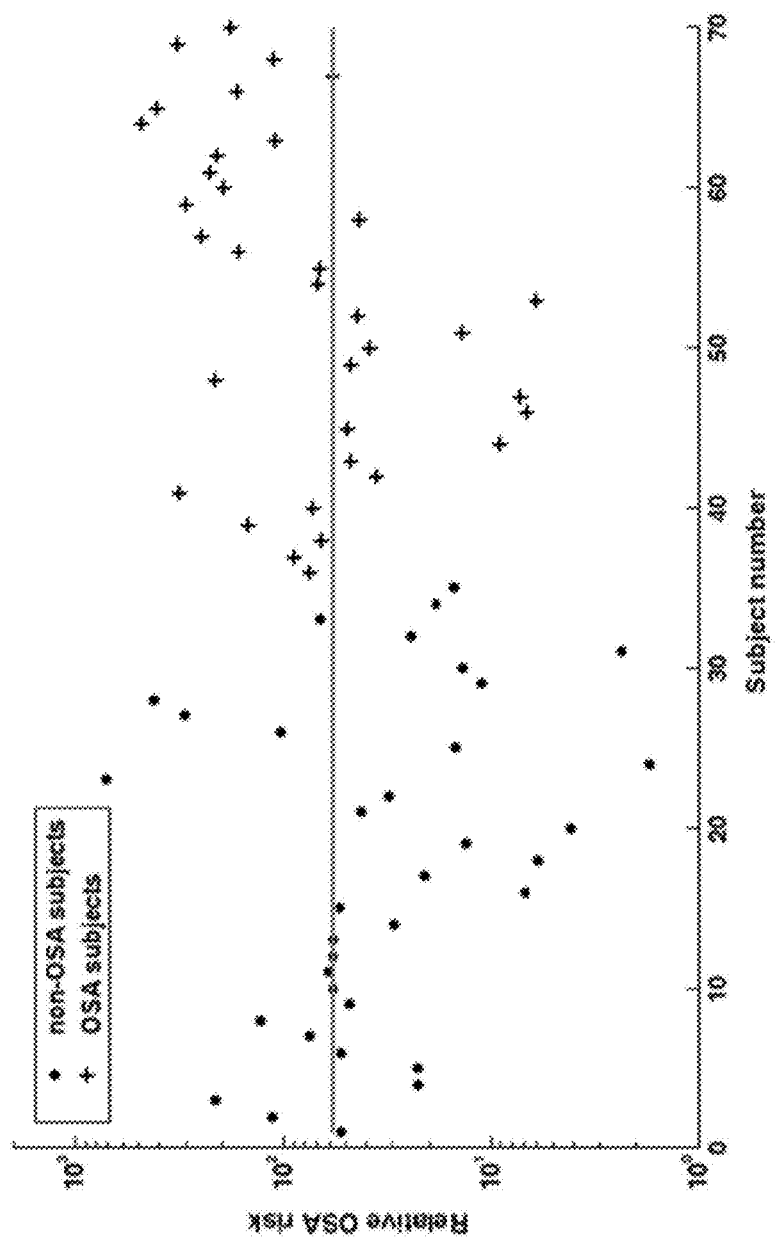
FIG. 6 is a plot showing relative OSA risk for the 70 subjects in a training dataset and the red horizontal line is the threshold used for classification.

FIG. 6 shows a plot of the relative risk of OSA using risk factors for the 70 subjects used in a training phase. As expected, on average non-OSA subjects have a lower relative risk compared to OSA group. A threshold of 58.4 (FIG. 6, horizontal line) resulted in the highest accuracy in separating the OSA and non-OSA groups in the training set. With this threshold, the accuracy, specificity, and sensitivity are 68%, 71%, and 66%, respectively. Applying the same threshold to classify the 87 subjects in the non-OSA (AHI<10) and OSA (AHI>20) groups not included in the training phase, the classification accuracy, specificity, and sensitivity were 68%, 76%, and 35% respectively. Considering the different number of non-OSA and OSA subjects in the testing dataset (70 versus 17), the overall accuracy was biased towards the specificity.

The 32 subjects in the middle group were classified based on relative risk and a threshold of 58.4. From the 16 subjects with 10≤AHI<15, 6 of them (38%) were classified as non-OSA (AHI<10) and 10 of them (62%) were classified as OSA (AHI>20). From the 16 subjects with 15<AHI≤20, 9 of them (56%) were classified as non-OSA (AHI<10) and 7 of them (44%) were classified as OSA (AHI>20). Therefore, it might be said that 38% of the subjects with 10≤AHI<15 and 44% of the subjects with 15<AHI≤20 were correctly classified and the overall accuracy was 41%.

Figure 7:
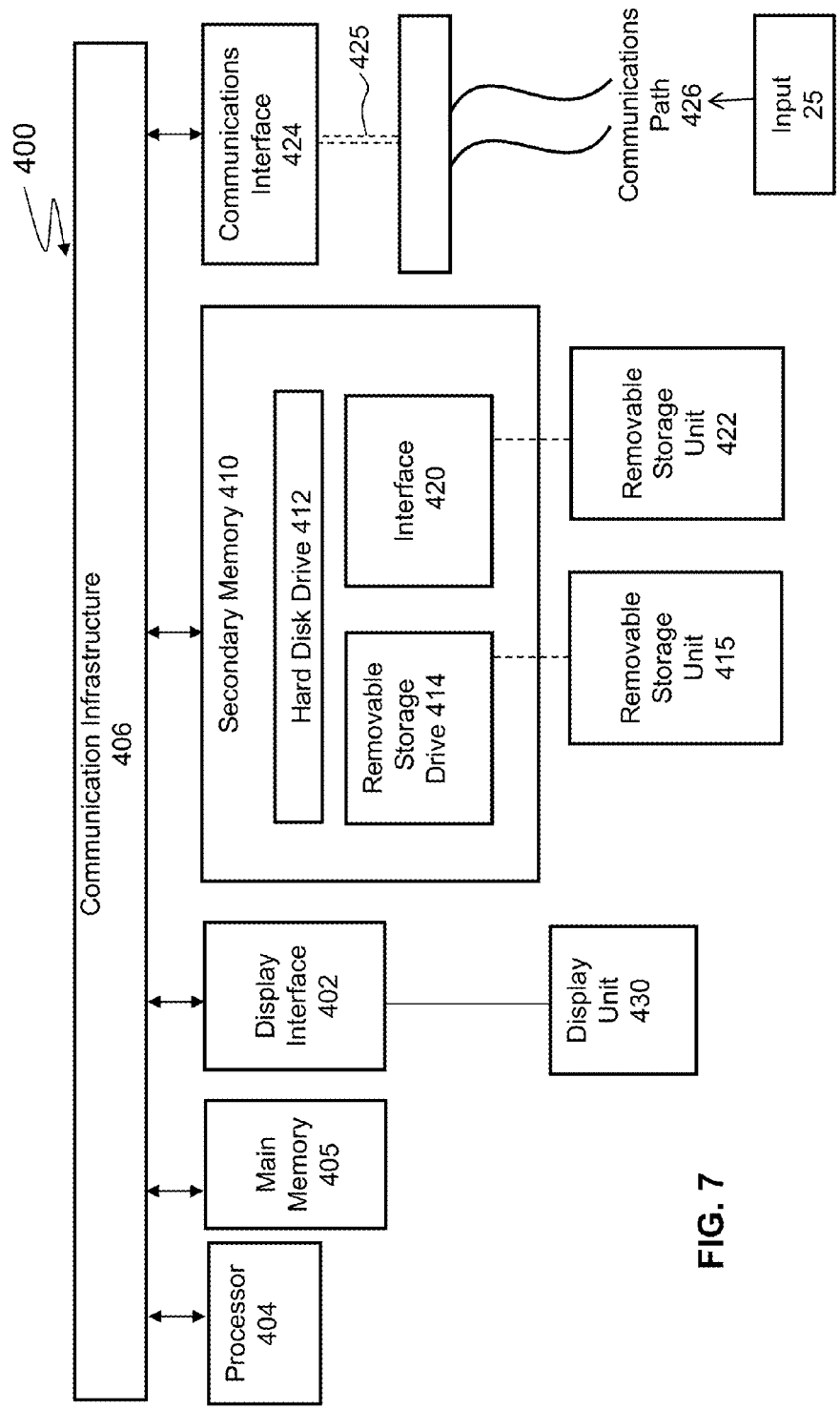
FIG. 7 is a schematic of a computer system for implementing the methods of the invention.

FIG. 7 illustrates an exemplary computer system 400, or network architecture, that may be used to implement certain methods according to the present invention. One or more computer systems 400 may carry out the methods presented herein as computer code. One or more processors, such as processor 404, which may be a special purpose or a general-purpose digital signal processor, is connected to a communications infrastructure 406 such as a bus or network. Computer system 400 may further include a display interface 402, also connected to communications infrastructure 406, which forwards information such as graphics, text, and data, from the communication infrastructure 406 or from a frame buffer (not shown) to display unit 430. Computer system 400 also includes a main memory 405, for example random access memory (RAM), read-only memory (ROM), mass storage device, or any combination thereof. Computer system 400 may also include a secondary memory 410 such as a hard disk drive 412, a removable storage drive 414, an interface 420, or any combination thereof. Computer system 400 may also include a communications interface 424, for example, a modem, a network interface (such as an Ethernet card), a communications port, a PCMCIA slot and card, wired or wireless systems, etc.

It is contemplated that the main memory 405, secondary memory 410, communications interface 424, or a combination thereof function as a computer usable storage medium, otherwise referred to as a computer readable storage medium, to store and/or access computer software and/or instructions.

Removable storage drive 414 reads from and/or writes to a removable storage unit 415. Removable storage drive 414 and removable storage unit 415 may indicate, respectively, a floppy disk drive, magnetic tape drive, optical disk drive, and a floppy disk, magnetic tape, optical disk, to name a few.

In alternative embodiments, secondary memory 410 may include other similar means for allowing computer programs or other instructions to be loaded into the computer system 400, for example, an interface 420 and a removable storage unit 422. Removable storage units 422 and interfaces 420 allow software and instructions to be transferred from the removable storage unit 422 to the computer system 400 such as a program cartridge and cartridge interface (such as that found in video game devices), a removable memory chip (such as an EPROM, or PROM) and associated socket, etc.

Communications interface 424 allows software and instructions to be transferred between the computer system 400 and external devices. Software and instructions transferred by the communications interface 424 are typically in the form of signals 425 which may be electronic, electromagnetic, optical or other signals capable of being received by the communications interface 424. Signals 425 are provided to communications interface 424 via a communications path 426. Communications path 426 carries signals 425 and may be implemented using wire or cable, fiber optics, a phone line, a cellular phone link, a Radio Frequency ("RE") link or other communications channels.

Computer programs, also known as computer control logic, are stored in main memory 405 and/or secondary memory 410. Computer programs may also be received via communications interface 424. Computer programs, when executed, enable the computer system 400, particularly the processor 404, to implement the methods according to the present invention. The methods according to the present invention may be implemented using software stored in a computer program product and loaded into the computer system 400 using removable storage drive 414, hard drive 412 or communications interface 424. The software and/or computer system 400 described herein may perform any one of, or any combination of, the steps of any of the methods presented herein. It is also contemplated that the methods according to the present invention may be performed automatically, or may be invoked by some form of manual intervention.

The sound input device 32, patient input, and optionally, a patient position mechanism—that is, a mechanism capable of detecting and exchanging information about the patient position with a computer system—may connect to the system 400 at the communications path 426 and provide input to the system 400. However, it is envisioned that in other embodiments, such elements may be connected at other parts of the system 400 as is known to those skilled in the art.

The invention is also directed to computer products, otherwise referred to as computer program products, to provide software to the computer system 400. Computer products store software on any computer useable medium. Such software, when executed, implements the methods according to the present invention. Embodiments of the invention employ any computer useable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The computer system 400, or network architecture, of FIG. 7 is provided only for purposes of illustration, such that the present invention is not limited to this specific embodiment. It is appreciated that a person skilled in the relevant art knows how to program and implement the invention using any computer system or network architecture.

Figure 8:
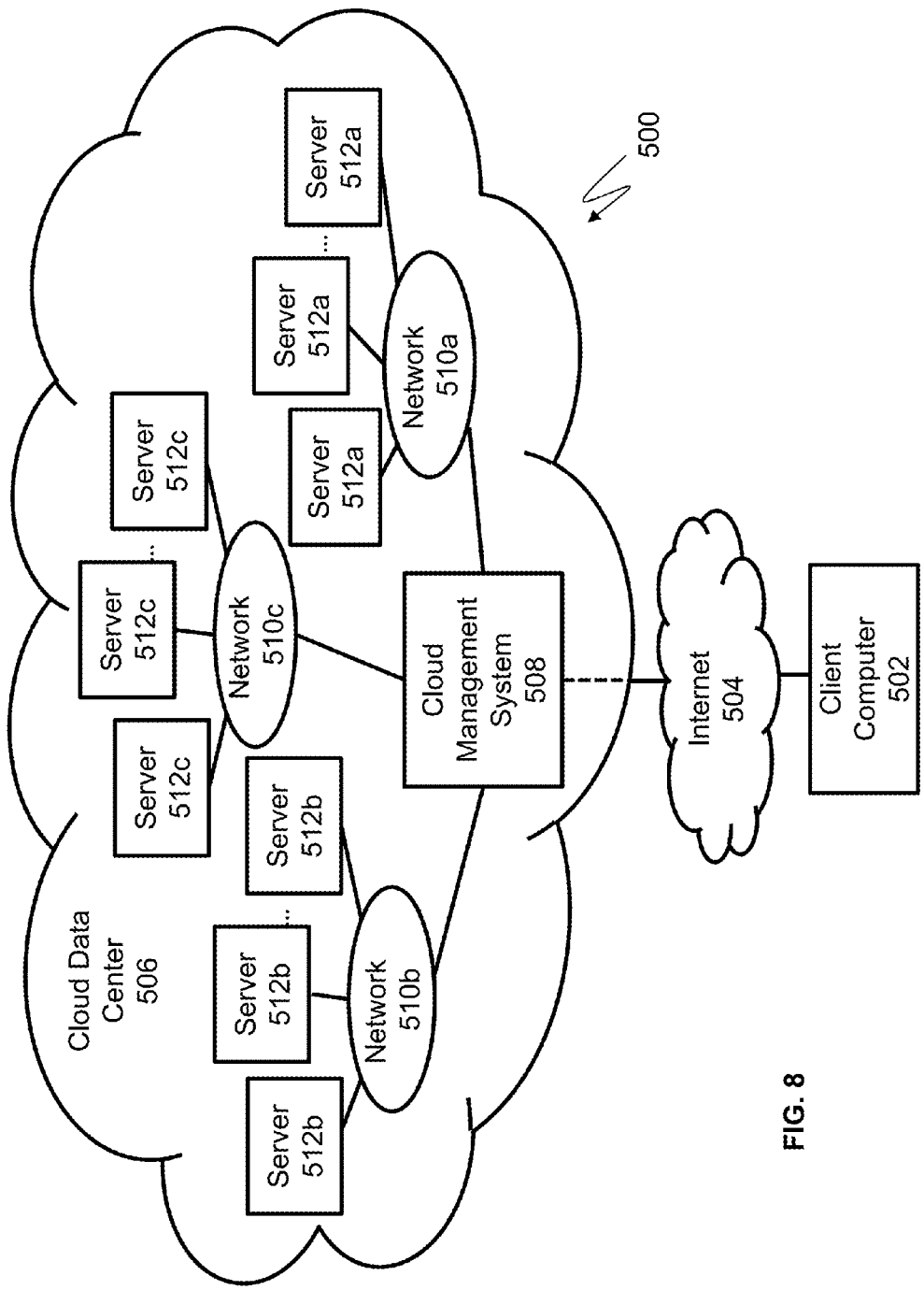

FIG. 8 illustrates an exemplary cloud computing system 500 that may be used to implement the methods according to the present invention. The cloud computing system 500 includes a plurality of interconnected computing environments. The cloud computing system 500 utilizes the resources from various networks as a collective virtual computer, where the services and applications can run independently from a particular computer or server configuration making hardware less important. Cloud computing embodiments may be configured to include security elements to comply with relevant privacy laws and standards. Other embodiments are configured to deliver system information to a user, but does not send or save the user's information via the cloud.

Specifically, the cloud computing system 500 includes at least one client computer 502. The client computer 502 may be any device through the use of which a distributed computing environment may be accessed to perform the methods disclosed herein, for example, a traditional computer, portable computer, mobile phone, personal digital assistant, tablet to name a few. The client computer 502 includes memory such as random access memory ("RAM"), read-only memory ("ROM"), mass storage device, or any combination thereof. The memory functions as a computer usable storage medium, otherwise referred to as a computer readable storage medium, to store and/or access computer software and/or instructions.

The client computer 502 also includes a communications interface, for example, a modem, a network interface (such as an Ethernet card), a communications port, a PCMCIA slot and card, wired or wireless systems, etc. The communications interface allows communication through transferred signals between the client computer 502 and external devices including networks such as the Internet 504 and cloud data center 506. Communication may be implemented using wireless or wired capability such as cable, fiber optics, a phone line, a cellular phone link, radio waves or other communication channels.

The client computer 502 establishes communication with the Internet 504—specifically to one or more servers—to, in turn, establish communication with one or more cloud data centers 506. A cloud data center 506 includes one or more networks 510a, 510b, 510c managed through a cloud management system 508. Each network 510a, 510b, 510c includes resource servers 512a, 512b, 512c, respectively. Servers 512a, 512b, 512c permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 508 can comprise a dedicated or centralized server and/or other software, hardware, and network tools to communicate with one or more networks 510a, 510b, 510c, such as the Internet or other public or private network, with all sets of resource servers 512a, 512b, 512c. The cloud management system 508 may be configured to query and identify the computing resources and components managed by the set of resource servers 512a, 512b, 512c needed and available for use in the cloud data center 506. Specifically, the cloud management system 508 may be configured to identify the hardware resources and components such as type and amount of processing power, type and amount of memory, type and amount of storage, type and amount of network bandwidth and the like, of the set of resource servers 512a, 512b, 512c needed and available for use in the cloud data center 506. Likewise, the cloud management system 508 can be configured to identify the software resources and components, such as type of Operating System ("OS"), application programs, and the like, of the set of resource servers 512a, 512b, 512c needed and available for use in the cloud data center 506.

The present invention is also directed to computer products, otherwise referred to as computer program products, to provide software to the cloud computing system 500. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The cloud computing system 500 of FIG. 8 is provided only for purposes of illustration and does not limit the invention to this specific embodiment. It is appreciated that a person skilled in the relevant art knows how to program and implement the invention using any computer system or network architecture.

The described embodiments are to be considered in all respects only as illustrative and not restrictive, and the scope of the present invention is not limited to the foregoing description. Those of skill in the art may recognize changes, substitutions, adaptations and other modifications that may nonetheless come within the scope of the present invention and range of the present invention. Each cited reference is incorporated by reference in its entirety.

REFERENCES

[1]. H. Peng, F. Long, and C. Ding, Feature selection based on mutual information: criteria of max-dependency, max-relevance, and min-redundancy," IEEE Transactions on pattern analysis and machine intelligence, pp. 1226{1238, 2005.

[2]. T. Young, E. Shahar, F. J. Nieto, S. Redline, A. B. Newman, D. J. Gottlieb, J. A. Walsleben, L. Finn, P. Enright, and J. M. Samet, "Predictors of sleep-disordered breathing in community-dwelling adults: the Sleep Heart Health Study," Arch Intern Med, vol. 162, pp. 893-900, 2002.

[3]. D. Wetter, T. Young, T. Bidwell, M. Badr, and M. Palta, "Smoking as a risk factor for sleep-disordered breathing," Arch Intern Med, vol. 154, pp. 2219-24, 1994.

[4]. T. Nuckton, D. Glidden, W. Browner, D. Claman, "Physical examination: Mallampati score as an independent predictor of obstructive sleep apnea," Sleep, vol. 29, 903-8, 2006.

[5]. X. Chen, X. Zhu, and D. Zhang, "A discriminant bispectrum feature for surface electromyogram signal classification," Med Eng Phys, vol. 32, pp. 126-135, 2010.

What is claimed is:

1. A method for screening a patient for obstructive sleep apnea during wakefulness comprising:
  (a) positioning a sound input device adjacent a suprasternal notch of a trachea of the patient;
  (b) recording tracheal breath sounds for at least five breathing cycles of the patient for each of nose breathing and mouth breathing with the patient in an upright position and at least five breathing cycles of the patient for each of nose breathing and mouth breathing with the patient in a supine position;
  (c) estimating power spectrum density (PSD) and bispectrum of the at least 5 breathing cycles for each of nose breathing and mouth breathing in the upright and the supine positions;
  (d) computing characteristic breathing sound features for the patient from the estimated PSD and the bispectrum of step (c), wherein the computed characteristic breathing sound features comprise a bispectral invariant P(a) defined by $$P(a)=a\,\tan(I_i(a)/I_r(a))$$

with at least one characteristic breathing sound feature selected from the group consisting of the bispectral invariant at 15° for inspiration phase of mouth breathing in upright posture, the bispectral invariant at 24° for inspiration phase of mouth breathing in upright posture, and the bispectral invariant at 27° for inspiration phase of mouth breathing in upright posture;

(e) comparing the value of the computed characteristic breathing sound features for the patient to mean values for corresponding features from a non-Obstructive Sleep Apnea (non-OSA) training set and an Obstructive Sleep Apnea (OSA) training set;

(f) classifying the patient as non-OSA or OSA based on the comparison of step (e); and (g) communicating to a user the classification of the patient as non-OSA or OSA.

2. The method of claim 1, further comprising at least four of the computed characteristic breathing sound features selected from the group consisting of: spectral centroid of mouth breathing in supine position, spectral centroid of mouth breathing in upright position, spectral bandwidth of nose breathing in upright position, spectral bandwidth of nose breathing in supine position, spectral bandwidth of mouth breathing in supine position, normalized bispectral squared entropy of mouth breathing in supine position, bispectral invariant of mouth breathing in upright position, relative signal power in upright position, spectral centroid in supine position, spectral centroid in upright position, normalized bispectral entropy in supine position, normalized bispectral entropy in upright position, bispectral invariant in upright position, signal power of mouth breathing in supine position, signal power of nose breathing in upright position, relative signal power of nose breathing in upright position, spectral centroid of nose breathing in upright position, spectral centroid of mouth breathing in upright position, median bi-frequency of nose breathing in upright position, and bispectral invariant of nose breathing in upright position.

3. The method of claim 1, wherein the computed characteristic breathing sound features further comprise:

I. Spectral centroid of PSD for the band of 450-600 Hz, for expiration phase of mouth breathing in upright posture II. Spectral bandwidth for the band of 1200-1800 Hz, for expiration phase of mouth breathing in supine posture III. Difference between nose and mouth breathing in spectral centroid for the band of 100-2500 Hz, for expiration phase in supine posture IV. Difference between supine and upright postures in signal power for the band of 100-150 Hz, for inspiration phase of mouth breathing.

4. The method of claim 1, further using age, gender, BMI, Mallampati score, neck circumference, and smoking history of the patient to aid in classifying the patient as OSA or non-OSA.

5. The method of claim 1, further comprising confirming the classification of step (f) by subjecting the patient to polysomnography.

6. The method of claim 1, wherein the estimated PSD is in the frequency range of 100 Hz to 2500 Hz.

7. The method of claim 1, wherein the estimated bispectrum is in the frequency range of 100 Hz to 2500 Hz.

8. The method of claim 1, wherein the computed characteristic breathing sound features are signal power, spectral centroid, spectral bandwidth, spectral flatness and crest factor, and are computed over a frequency range of 100 Hz to 2500 Hz.

9. The method of claim 1, wherein the computed characteristic breathing sound features are signal power, spectral centroid and spectral bandwidth, and are computed in each of 100 to 150 Hz, 150 to 450 Hz, 450 to 600 Hz, 600 to 1200 Hz, 1200 to 1800 Hz and 1800 to 2500 Hz bandwidths.

10. The method of claim 1, wherein the at least 5 breathing cycles for each of nose breathing and mouth breathing in the upright position and the at least 5 breathing cycles for each of nose breathing and mouth breathing in the supine position are separated into inspiration and expiration cycles.

\* \* \* \* \*